United States Patent [19]

Le Martret et al.

[11] 4,450,167
[45] May 22, 1984

[54] 3-QUINOLINE CARBOXAMIDES HAVING ANXIOLYTIC ACTIVITY

[75] Inventors: Odile Le Martret, Paris; Daniel Humbert, Fontenay-sous-Bois; Peter F. Hunt, Gonesse, all of France

[73] Assignee: Roussel Uclaf, Paris, France

[21] Appl. No.: 398,575

[22] Filed: Jul. 15, 1982

[30] Foreign Application Priority Data

Jul. 17, 1981 [FR] France ........................... 81 13957

[51] Int. Cl.³ ............... A61K 31/47; C07D 215/54; C07D 215/56
[52] U.S. Cl. ..................... 424/258; 546/153; 546/169
[58] Field of Search ............... 546/156, 169; 424/258

[56] References Cited

U.S. PATENT DOCUMENTS

| | | | |
|---|---|---|---|
| 2,504,875 | 4/1950 | Price et al. | 546/153 |
| 2,504,896 | 4/1950 | Snyder et al. | 546/156 X |
| 2,614,121 | 10/1952 | Price et al. | 546/156 X |
| 2,798,070 | 7/1957 | Cain | 546/169 |
| 3,960,868 | 6/1976 | Ferrini et al. | 424/258 X |
| 3,992,540 | 11/1976 | Clemence et al. | 424/258 |
| 4,107,310 | 8/1978 | Allais et al. | 424/258 |
| 4,299,831 | 11/1981 | Clemence et al. | 424/251 |

FOREIGN PATENT DOCUMENTS 0012369 6/1980 European Pat. Off. ........... 424/258

OTHER PUBLICATIONS

Price, J. Am. Chem. Soc., vol. 68, pp. 1251-1252, (1946).
Nagano, Chemical Abstracts, vol. 55, 11413f-i, (1961).
Moszew, et al., Chemical Abstracts, vol. 66, 28477x and 28624t, (1967).
Chakravorti, et al., Chemical Abstracts, vol. 72, 12529d, (1970).
Ridgway, et al., Chemical Abstracts, vol. 81, 169547s, (1974).
Kaminsky, Chemical Abstracts, vol. 72, 90322v, (1970).

Primary Examiner—Donald G. Daus
Assistant Examiner—Diana G. Rivers
Attorney, Agent, or Firm—Charles A. Muserlian

[57] ABSTRACT

Novel 3-quinoline-carboxamides of the formula

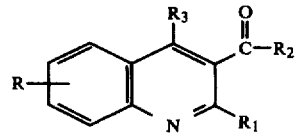

wherein R is in 6 or 7-position and is selected from the group consisting of hydrogen, halogen, alkyl of 1 to 6 carbon atoms, cycloalkyl of 3 to 6 carbon atoms, alkoxy of 1 to 6 carbon atoms, $-CF_3$, $-SCF_3$ and $CH_3S-$, $R_1$ is selected from the group consisting of hydrogen, alkyl of 1 to 6 carbon atoms, phenyl and benzyl, $R_2$ is $-NHR_4$, $R_4$ is selected from the group consisting of alkyl of 2 to 6 carbon atoms, substituted aryl of 6 to 10 carbon atoms and substituted heterocycle of an aromatic character of 3 to 5 carbon atoms with the proviso that when $R_4$ is a mono substituted aryl or heterocycle, the substituent is different from R of the quinoline when it is a halogen and $R_3$ is selected from the group consisting of hydrogen and $-OH$ and their non-toxic, pharmaceutically acceptable acid addition salts having remarkable anxiolytic properties capable of lessening emotional reactions and diminishing states of psychic tension and their preparation.

16 Claims, No Drawings

3-QUINOLINE CARBOXAMIDES HAVING ANXIOLYTIC ACTIVITY

STATE OF THE ART

French Pat. No. 960,299 describes quinolines of the formula

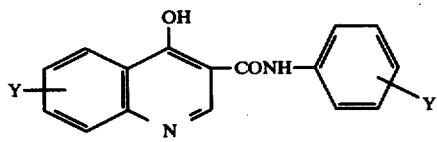

wherein a substituent having various values but no utility is given for the said compounds. French Pat. No. 2,002,888 describes some quinolines closely related to the compounds of formula I having antiviral properties.

OBJECTS OF THE INVENTION

It is an object of the invention to provide the novel quinolines of formula I and their non-toxic, pharmaceutically acceptable acid addition salts and a process for their preparation.

It is another object of the invention to provide novel anxiolytic compositions and a novel method of inducing anxiolytic activity in warm-blooded animals.

These and other objects and advantages of the invention will become obvious from the following detailed description.

THE INVENTION

The novel compounds of the invention are selected from the group consisting of 3-quinoline-carboxamides of the formula

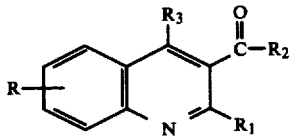

wherein R is in 6 or 7-position and is selected from the group consisting of hydrogen, halogen, alkyl of 1 to 6 carbon atoms, cycloalkyl of 3 to 6 carbon atoms, alkoxy of 1 to 6 carbon atoms, —$CF_3$, —$SCF_3$ and $CH_3S$—, $R_1$ is selected from the group consisting of hydrogen, alkyl of 1 to 6 carbon atoms, phenyl and benzyl, $R_2$ is —$NHR_4$, $R_4$ is selected from the group consisting of alkyl of 2 to 6 carbon atoms, substituted aryl of 6 to 10 carbon atoms and substituted heterocycle of an aromatic character of 3 to 5 carbon atoms with the proviso that when $R_4$ is a mono substituted aryl or heterocycle, the substituent is different from R of the quinoline when it is a halogen and $R_3$ is selected from the group consisting of hydrogen and —OH and their non-toxic, pharmaceutically acceptable acid addition salts.

Examples of halogens in the compounds of formula I are iodine, fluorine and preferably chlorine and bromind and alkyl of 1 to 6 carbon atoms include preferably methyl, ethyl, propyl, isopropyl and butyl. The cyclo alkyl of 3 to 6 carbon atoms is preferably cyclopropyl or cyclobutyl. The alkoxy of 1 to 6 carbon atoms is preferably methoxy, ethoxy, propoxy or butoxy. The preferred aryl of 6 to 10 carbon atoms is preferably phenyl and heterocycle of an aromatic character is preferably pyridyl and the aryl and heterocycle have at least one substituent selected from the group consisting of halogen, methyl, methoxy, methylthio, trifluoromethyl, trifluoromethylthio, —OH, —$NH_2$ and alkylamino and dialkylamino of 1 to 6 alkyl carbon atoms.

Examples of acids for the preparation of the non-toxic, pharmaceutically acceptable acid addition salts are inorganic acids such as hydrochloric acid, hydrobromic acid, nitric acid, sulfuric acid and phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and arylcarboxylic acids.

Among the preferred compounds of formula I are those wherein $R_4$ is substituted aryl, those wherein $R_3$ is —OH and those wherein $R_4$ is alkyl of 3 to 6 carbon atoms and their non-toxic, pharmaceutically acceptable acid addition salts.

Particularly preferred compounds of the invention are 4-hydroxy-N-(4-methoxyphenyl)-3-quinoline-carboxamide, 4-hydroxy-N-(4-hydroxyphenyl)-3-quinoline-carboxamide, 4-hydroxy-N-(3-methoxyphenyl)-3-quinoline-carboxamide, 4-hydroxy-N-n-propyl-3-quinoline-carboxamide, 4-hydroxy-N-n-butyl-3-quinoline-carboxamide and 4-hydroxy-N-n-hexyl-3-quinoline-carboxamide and their non-toxic, pharmaceutically acceptable acid addition salts.

The novel process of the invention for the preparation of the compounds of formula I comprises reacting a compound of the formula

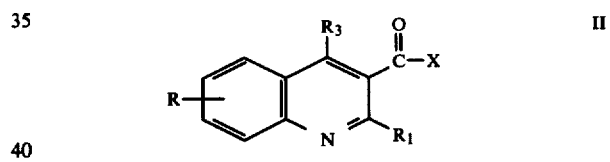

wherein R, $R_1$ and $R_3$ have the above definitions and X is selected from the group consisting of chlorine, hydroxy and ethoxy with a compound of the formula

$R_2$—H      III wherein $R_2$ has the above definition to obtain the corresponding compound of formula I which may be salified.

When X is chlorine, the reaction with the amine of formula III is effected in solution or suspension in inert solvents such as lower aliphatic ketones, dioxane, dimethylformamide, benzene and toluene and the reaction is preferably reacted in the presence of an acid acceptor such as alkali metal hydroxides like potassium hydroxide, alkali metal carbonates like potassium carbonate, alkali metal bicarbonates like sodium bicarbonate or potassium bicarbonate, alkali metal acetates, alkali metal alcoholates like sodium ethylate and preferably tertiary amines like pyridine and trialkylamines.

When X is ethoxy, the reaction with the amine of formula III is effected at reflux in a solvent with a boiling point of preferably 40° to 150° C. and the reflux may be maintained for 12 to 48 hours, for example. The reaction is preferably effected in the presence of a condensation agent such as an alkyl aluminum derivative like triisobutyl aluminum or trimethylaluminum. Also useful is the presence of traces of alkali metal hydrides such as sodium hydride or alkali metal alcoholates such as sodium ethylate or sodium tert.-butylate or aluminum isopropylate.

The compounds of formula I have a basic character and the acid addition salts thereof may be formed by reacting approximately stoichiometric proportions of the compound of formula I and the acid with or without isolation of the base.

The compounds of formula II are known and may be prepared by the process of French Pat. No. 2,340,735 and the amines of formula III are known.

The novel anxiolytic compositions of the invention are comprised of an anxiolytically effective amount of at least one compound of formula I and their non-toxic, pharmaceutically acceptable acid addition salts and an inert pharmaceutical carrier or excipient. The compositions may be in the form of tablets, dragees, gelules, granules, suppositories and injectable solutions or suspensions prepared in the usual manner.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

Among the preferred compositions of the invention are those containing the compounds of formula I wherein $R_4$ is substituted aryl, those wherein $R_3$ is —OH and those wherein $R_4$ is alkyl of 3 to 6 carbon atoms and their non-toxic, pharmaceutically acceptable acid addition salts.

Particularly preferred compounds of the invention are 4-hydroxy-N-(4-methoxyphenyl)-3-quinoline-carboxamide, 4-hydroxy-N-(4-hydroxyphenyl)-3-quinoline-carboxamide, 4-hydroxy-N-(3-methoxyphenyl)-3-quinoline-carboxamide, 4-hydroxy-N-n-propyl-3-quinoline-carboxamide, 4-hydroxy-N-n-butyl-3-quinoline-carboxamide and 4-hydroxy-N-n-hexyl-3-quinoline-carboxamide and their non-toxic, pharmaceutically acceptable acid addition salts.

The compositions of the invention due to their anxioloytic activity are useful for the treatment of anxiety states such as chronic anxiety associated or not with insomnia or behavior problems, anguish in adults or children or as a complement for treatment with neuroleptics or antidepressants of psychotic or depressive states.

The novel method of the invention for inducing anxiolytic activity in warm-blooded animals, including humans, comprises administering to warm-blooded animals an anxiolytically effective amount of at least one compound of formula I and their non-toxic, pharmaceutically acceptable acid addition salts. The compounds may be administered orally, rectally or parenterally and the usual daily dose is depending on the compound used and the condition being treated. For example, the compound of Example 6 is used at an oral daily dose of 0,015 to 1,5 mg/kg in humans to treat chronic anxiety.

In the following examples there are described several preferred embodiments to illustrate the invention. However, it should be understood that the invention is not intended to be limited to the specific embodiments.

EXAMPLE 1

4-hydroxy-N-(4-ethoxyphenyl)-3-quinoline-carboxamide 1.86 g of phenetidine were added to a suspension of 3 g of 4-hydroxy-3-quinoline-carboxylic acid chloride (described in French Pat. No. 2,340,735) in 40 ml of anhydrous pyridine and the mixture was stirred for 16 hours. 50 ml of aqueous 2 N hydrochloric acid solution were added to the mixture which was stirred for one hour and then was filtered. The recovered product was washed with water, dried at 180° C. under reduced pressure and was crystallized from 30 ml of acetic acid and then 10 ml of dimethylformamide to obtain 2.1 g of 4-hydroxy-N-(4-ethoxyphenyl)-3-quinoline-carboxamide in the form of crystals melting at 288° C.

Analysis: $C_{18}H_{16}N_2O_3$; molecular weight=308.34

Calculated: %C: 70.12; %H: 5.23; %N: 9.09; Found: %C: 69.9; %H: 5.1; %N: 9.1.

EXAMPLE 2

Using the procedure of Example 1, 4-hydroxy-3-quinoline-carboxylic acid chloride and 4-chloro-aniline were reacted to obtain after crystallization from acetic acid 4-hydroxy-N-(4-chlorophenyl)-3-quinoline-carboxamide melting at 344° C.

Analysis: $C_{16}H_{11}N_2O_2Cl$; molecular weight=298.731

Calculated: %C: 64.33; %H: 3.71; %N: 9.38; %Cl: 11.87; Found: %C: 64.0; %H: 3.6; %N: 9.2; %Cl: 12.1.

EXAMPLE 3

Using the procedure of Example 1, 4-hydroxy-3-quinoline-carboxylic acid chloride and 4-ethoxycarbonyl-aniline were reacted to obtain after crystallization from acetic acid 4-hydroxy-N-(4-ethoxycarbonylphenyl)-3-quinoline-carboxamide melting at 309° C.

Analysis: $C_{19}H_{16}N_2O_4$; molecular weight=336.357

Calculated: %C: 67.85; %H: 4.79; %N: 8.33; Found: %C: 67.6; %H: 4.8; %N: 8.2.

EXAMPLE 4

Using the procedure of Example 1 4-hydroxy-3-quinoline-carboxylic acid chloride and 3-trifluoromethyl-aniline were reacted to obtain after crystallization from acetic acid 4-hydroxy-N-(3-trifluoromethylphenyl)-3-quinoline-carboxamide melting at 323° C.

Analysis: $C_{17}H_{11}N_2F_3O_2$; molecular weight=332.284

Calculated: %C: 61.45; %H: 3.34; %N: 8.43; %F: 17.15; Found: %C: 61.3; %H: 3.3; %N: 8.3; %F: 17.0.

EXAMPLE 5

Using the procedure of Example 1, 4-hydroxy-3-quinoline-carboxylic acid chloride and 4-(dimethylamino)-aniline were reacted to obtain after crystallization from acetic acid 4-hydroxy-N-(4-dimethylaminophenyl)-3-quinoline-carboxamide melting at 336° C.

Analysis: $C_{18}H_{17}N_3O_2$; molecular weight=307.354

Calculated: %C: 70.34; %H: 5.58; %N: 13.67; Found: %C: 70.0; %H: 5.5; %N: 13.5.

EXAMPLE 6

Using the procedure of Example 1, 4-hydroxy-3-quinoline-carboxylic acid chloride and 4-methoxy-aniline were reacted to obtain after crystallization from acetic acid 4-hydroxy-N-(4-methoxyphenyl)-3-quinoline-carboxamide melting at 325° C.

Analysis: $C_{17}H_{14}N_2O_3$; molecular weight=294.310

Calculated: %C: 69.38; %H: 4.79; %N: 9.52; Found: %C: 69.5; %H: 4.8; %N: 9.5.

EXAMPLE 7

Using the procedure of Example 1, 4-hydroxy-3-quinoline-carboxylic acid chloride and 4-hydroxy-aniline were reacted to obtain after crystallization from ammonium hydroxide 4-hydroxy-N-(4-hydroxyphenyl)-3-quinoline-carboxamide melting at 365° C.

Analysis: $C_{16}H_{12}N_2O_3$; molecular weight=280.285
Calculated: %C: 68.57; %H: 4.32; %N: 9.99; Found: %C: 68.1; %H: 4.3; %N: 9.8.

EXAMPLE 8

Using the procedure of Example 1, 4-hydroxy-3-quinoline-carboxylic acid chloride and ethylamine were reacted to obtain after crystallization from ethanol 4-hydroxy-N-ethyl-3-quinoline-carboxamide melting at 236° C.

Analysis: $C_{12}H_{12}N_2O_2$; molecular weight=216.24
Calculated: %C: 66.65; %H: 5.59; %N: 12.95; Found: %C: 66.4; %H: 5.5; %N: 12.6.

EXAMPLE 9

Using the procedure of Example 1, 4-hydroxy-3-quinoline-carboxylic acid chloride and n-butyl-amine were reacted to obtain after crystallization from methanol 4-hydroxy-N-butyl-3-quinoline-carboxamide melting at 190° C.

Analysis: $C_{14}H_{16}N_2O_2$; molecular weight=244.29
Calculated: %C: 68.83; %H: 6.6; %N: 11.46; Found: %C: 69.0; %H: 6.7; %N: 11.4.

EXAMPLE 10

Using the procedure of Example 1, 4-hydroxy-3-quinoline-carboxylic acid chloride and n-hexyl-amine were reacted to obtain after crystallization from ethyl acetate 4-hydroxy-N-n-hexyl-3-quinoline-carboxamide melting at 160° C.

Analysis: $C_{16}H_{20}N_2O_2$; molecular weight=272.35
Calculated: %C: 70.56; %H: 7.40; %N: 12.28; Found: %C: 70.6; %H: 7.4; %N: 10.3.

EXAMPLE 11

4-hydroxy-N-(4-methoxyphenyl)-3-quinoline-carboxamide 230 ml of a toluene solution of triisobutyl aluminum were added with stirring at 8°-10° C. over 30 minutes to a mixture of 61.5 g of p-anisidine in one liter of anhydrous methylene chloride and then 21.7 g of ethyl 4-hydroxy-3-quinoline-carboxylate [described in J.A.C.S., Vol. 68 (1946), p. 1264] were added to the mixture in small portions. The mixture was refluxed for 20 hours and was evaporated to dryness. The residue was taken up in a mixture of 500 g of ice and 500 ml of aqueous 6 N hydrochloric acid and the mixture was stirred for 6 hours and vacuum filtered. The recovered product was washed with water until there were no chloride ions in the wash water, dried at 100° C. and was crystallized from acetic acid to obtain 23.54 g of 4-hydroxy-N-(4-methoxyphenyl)-3-quinoline-carboxamide melting at >260° C.

Analysis: $C_{17}H_{14}N_2O_3$; molecular weight=294.316
Calculated: %C: 69.38; %H: 4.79; %N: 9.52; Found: %C: 69.4; %H: 4.8; %N: 9.4.

EXAMPLE 12

Using the procedure of Example 11, ethyl 4-hydroxy-3-quinoline-carboxylate and 5-chloropyridylamine were reacted to obtain after crystallization from dimethylformamide and ether 4-hydroxy-N-(5-chloro-pyrid-2-yl)-3-quinoline-carboxamide melting at >260° C.

Analysis: $C_{15}H_{10}ClN_3O_2$; molecular weight=299.72
Calculated: %C: 60.11; %H: 3.36; %N: 14.02; %Cl: 11.83; Found: %C: 59.8; %H: 3.3; %N: 14.1; %C: 11.9.

EXAMPLE 13

Using the procedure of Example 11, ethyl 4-hydroxy-3-quinoline-carboxylate and 2-methoxy-aniline were reacted to obtain after crystallization from acetic acid and ether 4-hydroxy-N-(2-methoxy-phenyl)-3-quinoline-carboxamide melting at 260° C.

Analysis: $C_{17}H_{14}N_2O_3$; molecular weight=294.31
Calculated: %C: 69.38; %H: 4.79; %N: 9.52; Found: %C: 69.3; %H: 4.8; %N: 9.4.

EXAMPLE 14

Using the procedure of Example 11, ethyl 4-hydroxy-3-quinoline-carboxylate and 3,4-dimethoxy-aniline were reacted to obtain after crystallization from ethanol and ether 4-hydroxy-N-(3,4-dimethoxyphenyl)-3-quinoline-carboxamide melting at 240° C.

Analysis: $C_{18}H_{16}N_2O_4$; molecular weight=324.34
Calculated: %C: 66.66; %H: 4.97; %N: 8.63; Found: %C: 66.5; %H: 5.0; %N: 8.5.

EXAMPLE 15

Using the procedure of Example 11, ethyl 4-hydroxy-3-quinoline-carboxylate and 3,5-dichloro-pyridyl-2-amine were reacted to obtain after crystallization from acetic acid 4-hydroxy-N-(3,5-dichloro-pyrid-2-yl)-3-quinoline-carboxamide melting at 260° C.

Analysis: $C_{15}H_9Cl_2N_3O_2$; molecular weight=334.16
Calculated: %C: 53.91; %H: 2.71; %N: 12.57; %Cl: 21.22; Found: %C: 53.9; %H: 2.7; %N: 12.5; %Cl: 21.0.

EXAMPLE 16

Using the procedure of Example 11, ethyl 4-hydroxy-3-quinoline-carboxylate and 3-methoxyaniline were reacted to obtain after crystallization from acetic acid 4-hydroxy-N-(3-methoxy-phenyl)-3-quinoline-carboxamide melting at >260° C.

Analysis: $C_{17}H_{14}N_2O_3$; molecular weight=294.31
Calculated: %C: 69.38; %H: 4.79; %N: 9.52; Found: %C: 69.1; %H: 4.8; %N: 9.6.

EXAMPLE 17

Using the procedure of Example 11, ethyl 3-quinoline-carboxylate and 4-methoxy-aniline were reacted to obtain after crystallization from methanol N-(4-methoxy-phenyl)-3-quinoline-carboxamide melting at 194° C.

Analysis: $C_{17}H_{14}N_2O_2$; molecular weight=278.31
Calculated: %C: 73.36; %H: 5.07; %N: 10.06; Found: %C: 73.3; %H: 5.0; %N: 9.9.

EXAMPLE 18

Using the procedure of Example 11, ethyl 4-hydroxy-2-methyl-3-quinoline-carboxylate and ethylamine were reacted to obtain after crystallization from acetonitrile 4-hydroxy-N-ethyl-2-methyl-3-quinoline-carboxamide melting at 226° C.

Analysis: $C_{13}H_{14}N_2O_2$; molecular weight=230.269
Calculated: %C: 67.81; %H: 6.13; %N: 12.16; Found: %C: 67.8; %H: 6.1; %N: 12.2.

EXAMPLE 19

STEP A: Ethyl 4-chlorophenyl-aminomethylene-propanedioate

A mixture of 50 g of 4-chloro-aniline and 89 g of ethyl ethoxymethylenemalonate was stirred under an inert atmosphere and was then heated to 160° C. while distilling the ethanol formed. The mixture was cooled to obtain ethyl 4-chlorophenyl-aminomethylene-propanedioate in the form of an oil which was used as is for Step B.

STEP B: Ethyl 4-hydroxy-6-chloro-3-quinoline-carboxylate

A mixture of oil of Step A and 70 ml of phenyl oxide was stirred under an inert atmosphere and was then heated at 250° C. for one hour while distilling the formed ethanol. The mixture was cooled and 30 ml of acetone were added. The mixture was vacuum filtered and the product was empasted with 30 ml of acetone and was dried and crystallized from ethanol to obtain 36 g of ethyl 4-hydroxy-6-chloro-3-quinoline-carboxylate melting at >260° C.

Analysis: $C_{12}H_{10}ClNO_3$; molecular weight=251.7
Calculated: %C: 57.27; %H: 4.00; %N: 5.56; %Cl: 14.08; Found: %C: 57.5; %H: 4.0; %N: 5.5; %Cl: 14.0.

Using the procedure of Example 11, ethyl 4-hydroxy-6-chloro-3-quinoline-carboxylate and 4-methoxy-aniline were reacted to obtain after crystallization from acetic acid 4-hydroxy-N-(4-methoxy-phenyl)-6-chloro-3-quinoline-carboxamide melting at >260° C.

Analysis: $C_{17}H_{13}ClN_2O_3$; molecular weight=238.75
Calculated: %C: 62.11; %H: 3.99; %N: 8.52; %Cl: 10.78; Found: %C: 62.1; %H: 4.0; %N: 8.6; %Cl: 10.9.

EXAMPLE 20

Using the procedure of Steps A and B of Example 19, 3-methoxy-aniline and ethyl ethoxymethylenemalonate were reacted to obtain ethyl 4-hydroxy-7-methoxy-3-quinoline-carboxylate melting at >260° C.

Analysis: $C_{13}H_{13}NO_4$; molecular weight=247.31
Calculated: %C: 63.15; %H: 5.3; %N: 5.66; Found: %C: 63.1; %H: 5.4; %N: 5.7.

Using the procedure of Example 11, ethyl 4-hydroxy-7-methoxy-3-quinoline-carboxylate and 4-methoxy-aniline were reacted to obtain after crystallization from acetic acid 4-hydroxy-N-(4-methoxy-phenyl)-7-methoxy-3-quinoline-carboxamide melting at >260° C.

Analysis: $C_{18}H_{16}N_2O_4$; molecular weight=324.34
Calculated: %C: 66.65; %H: 4.97; %N: 8.63; Found: %C: 66.7; %H: 5.0; %N: 8.6.

EXAMPLE 21

Using the procedure of Example 11, ethyl 4-hydroxy-2-ethyl-3-quinoline-carboxylate and 4-methoxy-aniline were reacted to obtain after crystallization from acetonitrile 4-hydroxy-N-(4-methoxyphenyl)-2-ethyl-3-quinoline-carboxamide melting at 236° C.

Analysis: $C_{19}H_{18}N_2O_3$; molecular weight=322.366
Calculated: %C: 70.79; %H: 5.63; %N: 8.69; Found: %C: 70.9; %H: 5.9; %N: 8.4.

EXAMPLE 22

Using the procedure of Example 11, ethyl 4-hydroxy-2-ethyl-3-quinoline-carboxylate and ethylamine were reacted to obtain after crystallization from ethyl acetate 4-hydroxy-N-ethyl-2-ethyl-3-quinoline-carboxamide melting at 200° C.

Analysis: $C_{14}H_{16}N_2O_2$; molecular weight=244.296
Calculated: %C: 68.83; %H: 6.60; %N: 11.47; Found: %C: 68.8; %H: 6.7; %N: 11.2.

EXAMPLE 23

4-hydroxy-N-(4-methoxyphenyl)-2-methyl-3-quinoline-carboxamide

Using the procedure of Example 11, ethyl 4-hydroxy-2-methyl-3-quinoline-carboxylate [described in J. Het. Chem., Vol. 16 (1979), p. 1605] and p-anisidine in xylene were refluxed for 24 hours to obtain 4-hydroxy-N-(4-methoxyphenyl)-2-methyl-3-quinoline-carboxamide melting at 222° C.

EXAMPLE 24

4-hydroxy-N-propyl-3-quinoline-carboxamide

A suspension of 2.17 g of ethyl 4-hydroxy-3-quinoline-carboxylate in 20 ml of propylamine in the presence of traces of sodium hydride was refluxed and then was stirred at 50° C. for 16 hours. The mixture was poured into water and the suspension was vacuum filtered. The product was washed with water, dried in an oven at 100° C. and was crystallized from methanol to obtain 1.1 g of 4-hydroxy-N-propyl-3-quinoline-carboxamide melting at 210° C.

Analysis: $C_{13}H_{14}N_2O_2$; molecular weight=230.26
Calculated: %C: 67.8; %H: 6.13; %N: 12.16; Found: %C: 67.8; %H: 6.2; %N: 12.0.

EXAMPLE 25

Tablets were prepared containing either 20 mg of 4-hydroxy-N-(4-methoxyphenyl)-3-quinoline-carboxamide or 50 mg of 4-hydroxy-N-(4-hydroxyphenyl)-3-quinoline-carboxamide and sufficient excipient of lactose, starch, talc and magnesium stearate for a final tablet weight of 100 mg.

PHARMACOLOGICAL STUDY

A. Affinity for benzodiazepine receptors

The test was inspired by Möhler et al [Science, No. 198 (1977), p. 849–851] in which the cortex was removed from the brains of male rats weighing an average of 150 g and homogenized at a ratio of 1 part by weight per 20 parts by volume of 0.32 M sucrose. The homogenized mixture was centrifuged at 1000 g for 10 minutes at 0° C. and the surnageant was centrifuged at 30,000 g for 20 minutes at 4° C. The culot was suspended in 20 volumes of Tris HCl 50 mM buffer with a pH of 7.4 and the suspension was centrifuged at 30,000 g for 20 minutes at 4° C. The resulting culot was suspended in 50 ml of Krebs Tris HCl buffered at a pH of 7.4 and 2 ml of the suspension was incubated at 0° C. for 30 minutes in the presence of $^3H$ Diazepam at a concentration of $10^{-9}$ moles with increasing concentration of the test product to determine the non-specific fixation with non-radioactive Diazepam at a concentration of $10^{-6}$ moles.

The incubated suspensions were filtered through a Whatman GF/C filter and the filters were washed twice with 5 ml of Krebs Tris HCl buffer at a pH of 7.4 not 0° C. The radioactivity of the filters was measured by liquid scintillation and the affinity of the test product for benzodiazepine receptors was expressed in $CI_{50}$ or the concentration inhibiting by 50% the specific bonding of $^3$H diapezam. The results are reported in Table I:

TABLE I

| Product of Example | CI$_{50}$ in n Moles/liter |
|---|---|
| 1 | 40 |
| 6 | 7.5 |
| 7 | 4.4 |
| 8 | 11 |
| 9 | 3.7 |
| 10 | 6.7 |
| 13 | 54 |
| 16 | 6.6 |
| 23 | 23 |
| 24 | 1.2 |

The results of Table I show that the compounds of the invention have a strong affinity for benzodiazepine receptors.

B. Acute toxicity

The DL$_0$ dose or the maximum dose at which no mice were dead on the 8th day was determined by oral administration of the test compounds to mice. The products of Examples 1 to 24 all had a LD$_0$ greater than 400 mg/kg.

Various modifications of the products and methods of the invention may be made without departing from the spirit or scope thereof and it is to be understood that the invention is intended to be limited only as defined in the appended claims.

What we claim is:

1. A compound selected from the group consisting of 3-quinoline-carboxamides of the formula

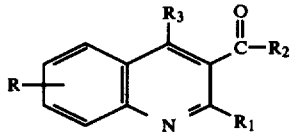

wherein R is in 6 or 7-position and is selected from the group consisting of hydrogen, halogen, and alkoxy of 1 to 6 carbon atoms R$_1$ is selected from the group consisting of hydrogen, alkyl of 1 to 6 carbon atoms, phenyl and benzyl, R$_2$ is —NHR$_4$, R$_4$ is alkyl of 2 to 6 carbon atoms, and R$_3$ is —OH and their non-toxic, pharmaceutically acceptable acid addition salts.

2. A compound of claim 1 selected from the group consisting of 4-hydroxy-N-n-propyl-3-quinoline-carboxamide and its non-toxic, pharmaceutically acceptable acid addition salts.

3. A compound of claim 1 selected from the group consisting of 4-hydroxy-N-n-butyl-3-quinoline-carboxamide and its non-toxic, pharmaceutically acceptable acid addition salts.

4. A compound of claim 1 selected from the group consisting of 4-hydroxy-N-n-hexyl-3-quinoline-carboxamide and its non-toxic, pharmaceutically acceptable acid addition salts.

5. An anxiolytic composition comprising an anxiolytically effective amount of at least one compound of claim 1 and a pharmaceutical carrier.

6. A composition of claim 5 wherein the compound is selected from the group consisting of 4-hydroxy-N-n-propyl-3-quinoline-carboxamide and its non-toxic, pharmaceutically acceptable acid addition salts.

7. A composition of claim 5 wherein the compound is selected from the group consisting of 4-hydroxy-N-n-butyl-3-quinoline-carboxamide and its non-toxic, pharmaceutically acceptable acid addition salts.

8. A composition of claim 5 wherein the compound is selected from the group consisting of 4-hydroxy-N-n-hexyl-3-quinoline-carboxamide and its non-toxic, pharmaceutically acceptable acid addition salts.

9. A method of inducing anxiolytic activity in warm-blooded animals comprising administering to warm-blooded animals an anxiolytically effective amount of at least one compound of 3-quinoline-carboxamides of the formula

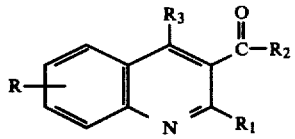

wherein R is in 6- or 7-position and is selected from the group consisting of hydrogen, halogen, alkyl of 1 to 6 carbon atoms, cycloalkyl of 3 to 6 carbon atoms, alkoxy of 1 to 6 atoms, —CF$_3$, —SCF$_3$ and CH$_3$S—, R$_1$ is selected from the group consisting of hydrogen, alkyl of 1 to 6 carbon atoms, phenyl and benzyl, R$_2$ is —NHR$_4$, R$_4$ is selected from the group consisting of alkyl of 2 to 6 carbon atoms, substituted aryl of 6 to 10 carbon atoms and substituted pyridyl, said substituents being at least one member of the group consisting of halogen, methyl, methoxy, methylthio, trifluoromethyl, trifluoromethylthio, —OH, —NH$_2$ and alkylamino and dialkylamino of 1 to 6 alkyl carbon atoms with the proviso that when R$_4$ is a mono substituted aryl or heterocycle, the substituent is different from R of the quinoline when it is a halogen and R$_3$ is selected from the group consisting of hydrogen and —OH and their non-toxic, pharmaceutically acceptable acid addition salts.

10. The method of claim 9 wherein in the compound, R$_4$ is substituted aryl.

11. A method of claim 9 wherein the compound is selected from the group consisting of 4-hydroxy-N-(4-methoxyphenyl)-3-quinoline-carboxamide and its non-toxic, pharmaceutically acceptable acid addition salts.

12. A method of claim 9 wherein the compound is selected from the group consisting of 4-hydroxy-N-(4-hydroxyphenyl)-3-quinoline-carboxamide and its non-toxic, pharmaceutically acceptable acid addition salts.

13. A method of claim 9 wherein the compound is selected from the group consisting of 4-hydroxy-N-(3-methoxyphenyl)-3-quinoline-carboxamide and its non-toxic, pharmaceutically acceptable acid addition salts.

14. A method of claim 9 wherein the compound is selected from the group consisting of 4-hydroxy-N-n-propyl-3-quinoline-carboxamide and its non-toxic, pharmaceutically acceptable acid addition salts.

15. A method of claim 9 wherein the compound is selected from the group consisting of 4-hydroxy-N-n-butyl-3-quinoline-carboxamide and its non-toxic, pharmaceutically acceptable acid addition salts.

16. A method of claim 9 wherein the compound is selected from the group consisting of 4-hydroxy-N-n-hexyl-3-quinoline-carboxamide and its non-toxic, pharmaceutically acceptable acid addition salts.

* * * * *